(12) United States Patent
Grof et al.

(10) Patent No.: US 11,508,195 B2
(45) Date of Patent: Nov. 22, 2022

(54) ACCESS CONTROL SYSTEM FOR UNLOCKING A LOCK MODULE, AND METHOD THEREOF

(71) Applicants: SOREQ NUCLEAR RESEARCH CENTER, Yavne (IL); SECURITY MATTERS LTD., D.N. Hevel Eilot (IL)

(72) Inventors: Yair Grof, Rehovot (IL); Tzemah Kislev, Mazkeret Bathya (IL); Nadav Yoran, Tel Aviv (IL); Haggai Alon, Kibbutz Naan (IL)

(73) Assignees: Soreq Nuclear Research Center, Yavne (IL); Security Matters Ltd., D.N. Revel Eilot (IL)

( * ) Notice: Subject to any disclaimer, the term of this patent is extended or adjusted under 35 U.S.C. 154(b) by 1108 days.

(21) Appl. No.: 16/083,966

(22) PCT Filed: Mar. 21, 2017

(86) PCT No.: PCT/IL2017/050354
§ 371 (c)(1),
(2) Date: Sep. 11, 2018

(87) PCT Pub. No.: WO2017/163242
PCT Pub. Date: Sep. 28, 2017

(65) Prior Publication Data
US 2020/0242865 A1    Jul. 30, 2020

Related U.S. Application Data
(60) Provisional application No. 62/310,936, filed on Mar. 21, 2016.

(51) Int. Cl.
*G07C 9/00* (2020.01)
*G06K 1/12* (2006.01)
(Continued)

(52) U.S. Cl.
CPC ......... *G07C 9/00571* (2013.01); *G01N 33/42* (2013.01); *G06K 1/126* (2013.01); *G06K 19/00* (2013.01)

(58) Field of Classification Search
CPC ...... G06K 19/00; G06K 1/126; G01N 23/223; G01N 33/42; G01N 23/2202;
(Continued)

(56) References Cited

U.S. PATENT DOCUMENTS

| 3,936,662 A | 2/1976 | Rausing |
| 7,753,272 B2 * | 7/2010 | Harper ................... G07C 9/00 235/382 |

(Continued)

FOREIGN PATENT DOCUMENTS

EP     1936539 A1    6/2008

*Primary Examiner* — Brian E Miller
(74) *Attorney, Agent, or Firm* — Browdy and Neimark, P.L.L.C.

(57) ABSTRACT

The present invention relates to an access control system, an access object and a method for access control. The access control system comprises an access request receiving device being configured and operable for receiving an access object; the access request receiving device comprising an emitter configured and operable for irradiating the access object with a radiation having a wavelength in the range of about 10"12 and 10"9 m and a detector configured and operable for detecting a response signal from the irradiated access object; a control circuit being configured and operable to receive the response signal from the access request receiving device and process the response signal to identify spectral features indicative of an XRF signature of the access object; wherein the control circuit is adapted to generate an unlocking signal for switching a module device between a locked state and an unlocked state upon identification of the XRF signature.

17 Claims, 5 Drawing Sheets

(51) Int. Cl.
*G01N 33/42* (2006.01)
*G06K 19/00* (2006.01)

(58) Field of Classification Search
CPC ....... G01N 2223/076; G01N 2223/652; G01N 2223/60; G07C 9/00571; G07C 9/00658
See application file for complete search history.

(56) References Cited

U.S. PATENT DOCUMENTS

| | | | |
|---|---|---|---|
| 7,999,659 B2 | 8/2011 | Friedrich | |
| 8,064,570 B2* | 11/2011 | Tannian | G01N 23/223 378/45 |
| 8,408,851 B2 | 4/2013 | Hadad | |
| 8,571,254 B2 | 10/2013 | Ogura | |
| 8,590,800 B2 | 11/2013 | Baque | |
| 8,864,038 B2 | 10/2014 | Marka et al. | |
| 10,539,521 B2* | 1/2020 | Grot | G01N 23/223 |
| 11,131,121 B2* | 9/2021 | Khlopkov | G07C 9/00182 |
| 2002/0097832 A1* | 7/2002 | Kaiser | G01N 23/223 378/45 |
| 2004/0114779 A1* | 6/2004 | Blazey | G07C 9/20 382/100 |
| 2009/0086905 A1* | 4/2009 | Boyden | G01N 23/223 378/46 |
| 2010/0077809 A1* | 4/2010 | Gerner | E05B 47/063 70/278.2 |
| 2013/0299591 A1* | 11/2013 | Marka | G06K 19/00 235/491 |
| 2014/0145823 A1 | 5/2014 | Aase | |
| 2017/0352216 A1* | 12/2017 | Donovan | G07C 9/29 |
| 2018/0293823 A1* | 10/2018 | Gil | H04W 12/50 |
| 2020/0242865 A1* | 7/2020 | Grof | G07C 9/00658 |
| 2021/0012278 A1* | 1/2021 | Alon | G06F 21/64 |

* cited by examiner

ACCESS CONTROL SYSTEM FOR UNLOCKING A LOCK MODULE, AND METHOD THEREOF

TECHNOLOGICAL FIELD

The present invention generally provides a novel technique for access control and key control.

BACKGROUND

Advanced access control methods for selective restriction of access rely on a piece of information (e.g. a PIN number, biometric identification data) which is presented to a reader at an access point. In such systems, the information/code is inputted via a keypad or it may be carried by a physical media such as swipe cards, RFID devices which are read by a reader installed at the point of access. The same types of systems and method are used in systems and methods for preventing unauthorized duplication of keys.

US Patent Application No. 2014/0145823 to Aase is directed to access control systems that utilize Near Field Communications (NFC)-enabled devices. The disclosed system enables an NFC device to be remotely checked-in to the access control system. The NFC device operates in a read/write mode rather than a card emulation mode when interacting with RFID readers of the access control system.

U.S. Pat. No. 8,408,851 to Hadad is directed to a method for duplicating a key including receiving a key identification code indicative of key cuts in an original key, and duplicating the original key by forming key cuts in a duplicate key in response to the key identification code, wherein authorization to form the key cuts is restricted by means of a verification code that must be passed before forming the key cuts is permissible. The authorization to form the key cuts may be restricted in various ways, such as to a group of users, a geographic location of a user, or a group of key blanks. The authorization to form the key cuts may be restricted as a function of a physical characteristic of the original key. As another alternative, authorization to form the key cuts may be restricted as a function of whether the original key is a master key or a slave key.

X-ray fluorescence (XRF) marking is a technique used to detect and possibly quantify chemical material elements and/or compositions constituents which can serve for marking an object. The parameters/identity of the object can then be identified based on the detected materials.

Counterfeiting and supply chain diversion of materials, are phenomena impacting many fields. Many materials of inferior quality, including but not limited to raw materials, electronics, polymers and pharmaceuticals are counterfeited by manufacturers and enter the supply chain, often by copying labeling associated with "brand" companies. To this end, there are various techniques known in the art which utilize XRF marking to identify object/materials and determine their source/manufacturer/owner and/or various parameter and thereby enabling to discern between the original materials/goods and counterfeit materials/goods. Since chemical makeup of the original and counterfeited materials may be similar, some techniques utilize additive XRF markers (such as compositions of materials having specific a-priory known XRF signature), which are specifically added to the object to enable identification of the object and/or certain parameters thereof such as its source.

For example, U.S. Pat. No. 8,590,800 discloses a method of authenticating and/or identifying an article containing a chemical marking agent, which is substantially inseparably enclosed in a marker as a carrier and contains selected chemical elements and/or compounds in the form of marker elements, in concentrations based on a predetermined encryption code, which method comprises the steps of: i) qualitatively and/or quantitatively identifying the marker elements of the chemical marking agent, and ii) comparing the values identified in step (i) with the predetermined encryption code.

U.S. Pat. No. 8,864,038 discloses a material tracing technique for encoding information in a material. The technique includes storing information to be encoded in the material, generating a number based on the information, determining an amount of at least one tracer to be incorporated into the material corresponding to the number, and incorporating the determined amount of the at least one tracer into the material. Decoding information encoded in the material includes measuring an amount of the at least one tracer, in some embodiments after tracer activation, determining a number corresponding to the measured at least one tracer, and decoding the number to obtain information associated with the material.

U.S. Pat. No. 7,999,659 discloses a method for access control to at least one memory area of a passive and/or backscatter-based transponder. In the method for access control, depending on an identification selection criterion, a first or at least one second identification within the transponder is activated, the activated identification upon an appropriate request by reader unit is transmitted to the unit, the at least one memory area of the transponder is divided into memory blocks with a settable size, access control information is assigned to a respective memory block, and read and/or write access to a specific memory block is released or blocked depending on the associated access control information and the identification selection criterion.

U.S. Pat. No. 8,571,254 discloses an authentication system including a measuring portion that radiates terahertz waves to a portable medium for authentication including materials having a characteristic oscillation frequency in a terahertz frequency band, measures a spectrum, and outputs a measurement spectrum that is a measurement result; a characteristic spectrum database which stores a characteristic spectrum of the materials; a discriminating portion that discriminates the materials that are included in the portable medium for authentication based on the measurement spectrum and the characteristic spectrum, and outputs a discrimination result.

General Description

The present invention relates to a novel access control technique. According to this technique, there is provided an access control system comprising an access request receiving device being configured and operable for receiving an access object; the access request receiving device comprising an emitter configured and operable for irradiating the access object with a radiation having a wavelength in the range of about $10^{-12}$ and $10^{-9}$ m and a detector configured and operable for detecting a response signal from the irradiated access object; a control circuit being configured and operable to receive the response signal from the access request receiving device and process the response signal to identify spectral features indicative of an XRF signature of the access object; wherein the control circuit is adapted to generate an unlocking signal for switching a module device between a locked state and an unlocked state upon identification of the XRF signature. The access request receiving device may be configured as X-ray fluorescence (XRF) reader, configured for reading access objects marked by XRF. In the following X-ray fluorescence (XRF) is used to refer to the emission of characteristic "secondary" (or fluorescent) X-rays from a material that has been excited by a primary X-ray or gamma-ray radiation. The term fluorescence refers absorption of radiation of a specific energy resulting with the re-emission of radiation of a different energy (typically lower).

The lock module is commonly used to hold lids, doors or other closure elements of boxes, safes, cabinets, doorways and other framed structures in closed and/or locked positions, and further typically is used to provide some measure of security against unauthorized or inadvertent access. The lock module may be an electrical, mechanical or electromechanical lock.

The technique of the present invention is associated with an access object (e.g. a key, an access card, a ticket) with one or more compounds that are appended to the access object and which may be detected or read by x-ray fluorescence (XRF). The access object may be metallic keys or key blanks, with or without plastic parts (such as handles, grips or covers), plastic cards, or paper cards/tickets. The novel access control technique of the invention is highly generic, insensitive to object materials and structure and thus permits verification of authenticity of a great variety of such objects, e.g., metallic keys or key blanks, with or without plastic parts (such as handles, grips or covers), plastic cards, or paper cards/tickets. The access object may be associated with personnel for which access should be granted or denied.

In some embodiments, the module device is a lock module operable between an unlocked state and a locked state and vice versa.

In some embodiments, at least one of the access request receiving device and the control circuit are at least partially disposed within the lock module.

In some embodiments, the access request receiving device is configured such that a distance between the access object received by the access request receiving device and the access request receiving device does not exceed 1 cm.

In some embodiments, the access control system further comprises a radiation absorbing element configured and operable to prevent emission of the radiation out of the access control system.

In some embodiments, the access control system further comprises a housing, wherein the control circuit, the access request receiving device, and the lock module are housed in the housing.

In some embodiments, the control circuit comprises a memory in which XRF signatures for the lock module are stored.

In some embodiments, the access control system further comprises a database for storing XRF signatures to which the control circuit includes access.

In some embodiments, the lock module includes a motor mechanically coupled to a latch mechanism for locking and unlocking the latch mechanism, thereby switching the lock module between the unlocked and locked state.

In some embodiments, the control circuit comprises a coupling member configured and operable to control the motor.

In some embodiments, the access control system further includes a processor coupled to the access control system. The processor is configured for modifying XRF signatures list associated with user access stored within the control circuit. The processor may be a part of the access control system or may be external to said access control system providing communication between the database and the lock module and modification/addition of signatures if required by the user.

In some embodiments, the lock module is adapted to secure a door.

In some embodiments, the lock module is integrated within a door.

In some embodiments, the lock module is adapted to fit within an aperture formed in a door for a standard mechanical lock.

In some embodiments, the access control system is connectable to a network with a host computer. The host computer is external to the control circuit.

In some embodiments, the access control system further comprises an access object having an XRF signature corresponding to a certain lock module.

In some embodiments, the access object is a key comprising a coded physical or electrical pattern for opening the lock module. The database includes data indicative of the coded physical or electrical pattern corresponding to a certain XRF signature.

In some embodiments, the control circuit is adapted to receive from the database, the data indicative of a correspondence between the coded pattern and the XRF signature, to thereby determine a match between the XRF signature and the pattern and upon determining the match switching the lock module between the unlocked and locked state.

In some embodiments, the access object comprises a first codable part adapted for carrying a coded physical or electrical pattern corresponding to a lock module, and a second codable part carrying at least one XRF marker embedded therein and defining the XRF signature to be matched with the lock module.

In some embodiments, the module device is an access object duplication assembly adapted to enable duplication of the coded physical or electrical pattern in the first codable part, upon receiving the unlocking signal generated by the control circuit.

According to another broad aspect of the present invention, there is provided an access object comprising a first codable part adapted for carrying a coded physical or electrical pattern corresponding to a lock module, and a second codable part carrying at least one XRF marker embedded therein and defining an XRF signature to be matched with the lock module to enable unlocking the lock module based on a matching between the coded physical or electrical pattern and the XRF signature.

In some embodiments, the access object comprises at least one of keys, key blanks, locks, access cards, access badges, tickets, and Id documents such as passports, identification cards.

In some embodiments, the access object comprises a metallic key having plastic grip, wherein the metallic key and the plastic grip has the same XRF signature.

In some embodiments, the XRF signature includes information about at least one of a depth of key cuts defining a key combination, physical characteristic of the key, configuration of a key profile.

In some embodiments, the access object is to be used with an access control system is defined above.

According to another broad aspect of the present invention, there is provided a method for access control comprising: irradiating an access object with radiation having a wavelength in the range of about $10^{-12}$ to $10^{-9}$ m; detecting a response signal from the irradiated access object; identifying in the response signal spectral features indicative of an XRF signature; and; generating an unlocking signal for switching a module device between a locked state and an unlocked state upon identification of the XRF signature.

In some embodiments, the method comprises enabling access upon identification of the XRF signature.

In some embodiments, the method comprises switching a lock module between an unlocked state and a locked state and vice versa.

In some embodiments, the method comprises modifying a XRF signatures list associated with user access.

In some embodiments, the method comprises securing a door.

In some embodiments, the method comprises receiving data indicative of a correspondence between a coded pattern carried by the access object and the XRF signature, to thereby determine a match between the XRF signature and the pattern.

In some embodiments, the method comprises preventing unauthorized key duplication upon identification of the XRF signature.

According to another broad aspect of the present invention, there is provided a key duplication machine applying the method as defined above.

BRIEF DESCRIPTION OF THE DRAWINGS

In order to better understand the subject matter that is disclosed herein and to exemplify how it may be carried out in practice, embodiments will now be described, by way of non-limiting example only, with reference to the accompanying drawings, in which.

DETAILED DESCRIPTION OF EMBODIMENTS

Figure 1A:
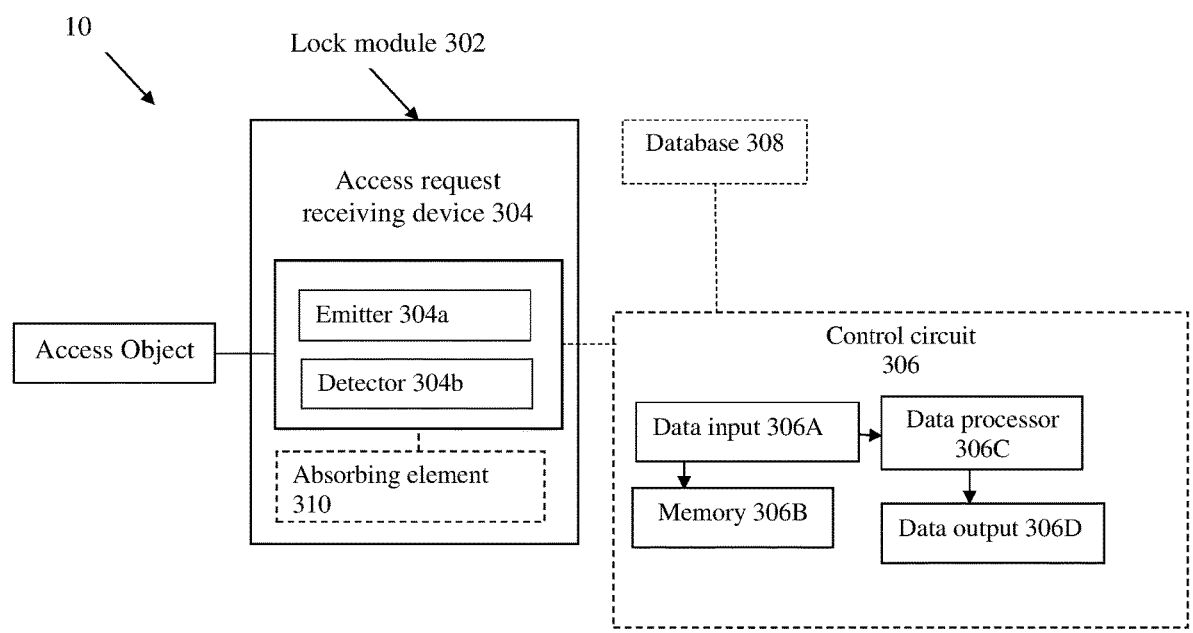
FIG. 1a is a schematic block diagram of an access system of the present invention.

Reference is made to FIG. 1a representing a block diagram of the access control system of the present invention. The system comprises a lock module 302 an access request receiving device 304 and a control circuit 306. The access request receiving device 304 and/or the control circuit 306 may be integrated or not within the lock module 302. The access request receiving device 304 is configured and operable for receiving an access object and comprises an emitter 304a comprising and operable for irradiating the access object with a radiation having a wavelength in the range of about $10^{-12}$ and $10^{-9}$ m and a detector 304b configured and operable for detecting a response signal from the irradiated access object. The access request receiving device 304 may be an XRF reader of any type known in the art such as disclosed for example in U.S. Provisional patent application No. 62/142,100 or in U.S. Provisional patent application No. 62/396,412 assigned to the assignee of the present invention which is incorporated herein by reference or in U.S. Pat. No. 6,501,823. Although for the sake of clarification, the radiation emitter 304a and the radiation detector 304b are represented as two separate physical elements, they can be integrated in the same physical element or in the same housing. To be enable to identify the XRF signature, the system 10 is configured such that, when the access object is inserted within the access request receiving device 304, the distance between the access object and the access request receiving device 304 does not exceed 1 cm. It should be also appreciated that the emitter and the detector can be placed anywhere at a certain distance from the access object to be inserted, on the lock module, on the wall next to the lock module, in elevators without a lock, gate controllers, etc.

The control circuit 306 is configured generally as a computing/electronic utility including inter alia such utilities as data input and output utilities 306A, 306B, memory 306C, and data processor module 306D. As will be described more specifically further below, the control circuit 306 is configured to receive and process the response signal emitted by the XRF coded access object and identify spectral features indicative of an XRF signature of the respective XRF coded access object. For example, the XRF signature may include information about the depth of the key cuts that define the key combination (such as to lift pins to a shear line in cylinder lock), as well as other information regarding a physical characteristic of the key, such as but not limited to, the configuration of the keyway profile. The information included in the XRF signature can be associated with the manufacturer and/or manufacturing process, for example date of manufacturing, serial number, client or destination of the object, date of shipment, type of key/access object, but it can also include more detailed information on the cutting process as suggested above.

The control circuit 306 may be a portable XRF analyzer. It should be noted that the access request receiving device 304 may be also portable and/or handheld device. In this configuration, the access request receiving device 304 is spaced-apart from the lock module 302. The access object is then interrogated by the access request receiving device 304 at some location which can be distant from the lock module and the response signal authenticating the access object is transmitted to the lock module 302 via wired/wireless connection or via a communication network. In some embodiments, the access control system is connectable to a communication network with a host computer, which host computer is external to the control circuit 306. Alternatively, the portable access request receiving device 304 can be also attached to the lock module 302 by using a coupling member of any type. The control circuit 306 is configured and operable to control access at an access point and for key control purposes. The control circuit 306 may be integrated within the lock module 302 or may be a separate element communicating with the access request receiving device 304 via wire or wireless communication. If the control circuit 306 is integrated within the lock module 302, identification of the access object does not require or employ any type of electronic components, circuitry or antenna. It is not shown in details, but should be appreciated that signal exchange and communication is enabled between the modules of the system by virtue of appropriate wiring or wirelessly. For example, the access request receiving device 304 and the control circuit 306 can be connected by IR (Infra-Red), RF (radio frequency including Bluetooth) or cable control. If the access request receiving device 304 and the control circuit 306 are integrated in the same physical housing, the XRF signature is stored in the control circuit 306. Access in such an embodiment is determined at the particular access point without communicating with additional system. It should be noted that such configuration maximizes security i.e. such system cannot be hacked by eavesdropping to the communication between the different components of the system.

The system 10 is configured to be used with an access object configured to be identifiable by XRF, such that upon examination by XRF analysis, authenticity of the access object may be verified and access to an access point may be allowed or denied. For example, the access object comprises an authentic key for which access should be allowed, having a preselected XRF signature. The XRF coded access object is incorporated in a general coding system wherein the identification of the access object is determined according to the preselected signature. Access rules and restrictions, as well as authorizations for various operations (e.g. duplication of a key) depend on the preselected signature of the access object. The preselected signature of the access objects can be used at the same time for a number of purposes, for example access control, key control and prevention of unauthorized duplication. The access object may be any object which is used for access or any component of an access control or key control system, such objects may be, for example, keys, key blanks, locks, access cards, access badges, tickets, and Id documents such as passports, identification cards. For example, the access object may be a commonly used metallic key which may or may not include plastic parts such as grips or covers. The access object may a card or an access badge (e.g. a plastic card or paper card). For example, the access object may comprise a metallic key having plastic grip or cover, may be marked by the same XRF signature on both its metallic surface and its plastic surface. Although the marking composition may be different for the different parts of the access object, the access object may include in addition to the markers other materials such as binders etching agents configured for marking the access object. The plastic surface may be a polymeric material made of thermoplastic polymer or thermosettic polymer. The plastic surface may be of one uniform polymer, or a blend of polymers, or a blend of co-polymers. The plastic surface may be made by casting or injection molding, or by Machining (CNC, engraving) vacuum casting, 3D printing, or vacuum forming. The polymeric matrix could be pure polymer, or with additives such as non-organic powders, fillers, pigments, flame retardants, with or without dispersant agents, with or without wetting agents, with or without surfactant agents, with or without stabilized agents, with or without anti-oxidant agents, with or without anti-uv agents. The access object may include additional identification and/or security features.

In some embodiments, the access object comprises a region carrying at least one XRF marker embedded therein and defining the XRF signature to be matched with the lock module. The presence of few XRF markers defining the XRF signature on the access object does not impede additional identification and/or security features if any. The access object may include together with the XRF signature, additional information in a magnetic or biometric form.

In some embodiments, the access object includes a marking composition as described for example in U.S. provisional patent application No. 62/290,146 which is incorporated herein by reference.

Figure 1B:
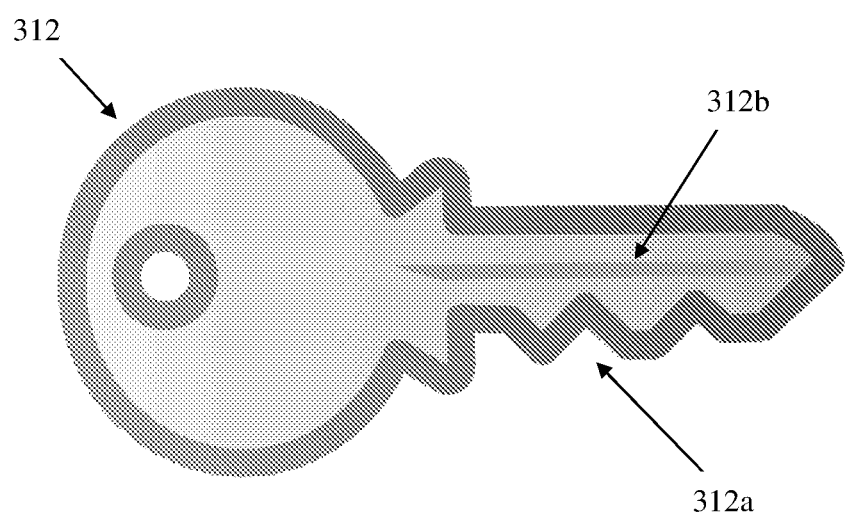
FIG. 1b is a schematic illustration of an access object of the present invention.

Reference is made to FIG. 1b illustrating an embodiment of the present invention in which the access object 312 is a key comprising a coded physical or electrical pattern for opening the lock module, wherein the coded physical or electrical pattern corresponds to a certain XRF signature. It should be noted that the certain XRF signature does not necessarily correspond to a single key/access object but may correspond to a group of keys/access objects. The XRF signature can also contain information which restricts access to some access objects (which would otherwise open the lock module) under certain conditions. For example, the information restricts access to some access objects according to a specific time period (e.g. day/night). The data indicative of such correspondence/matching is stored in a database external to internal to the system. The control circuit is then adapted to receive from the database, the data indicative of the correspondence between the coded pattern and the XRF signature, to thereby determine a match between the XRF signature and the pattern and upon determining the match switching the lock module between the unlocked and locked state. The access object comprises a first codable part 312a adapted for carrying the coded physical or electrical pattern corresponding to the lock module, and a second codable part 312b carrying at least one XRF marker embedded therein and defining the XRF signature to be matched with the lock module. The first and second codable parts may be separate or partially overlapping or completely overlapping physical regions of the access object. The matching between the coded physical or electrical pattern and the XRF signature enables unlocking the lock module 302.

The lock module 302 may be integrated within the access point.

The lock module 302 is associated with at least one matching access object enabling access to the access point. The access point may be a door or a passage to be accessed.

In an embodiment, the XRF signatures which allow access at an access point/lock module or a plurality of access points may be stored in a database 308 which may be managed or controlled by a host computer is external to the control circuit 306 or by the control circuit 306. Alternatively, the XRF signatures (e.g. codes associated with a lock module/access point) may be stored only in the lock module 302 or access point. The restriction on access for an access object or a group of access objects associated with an XRF signature can be controlled via the host computer. For example, access at a particular access point for an XRF signature may tightened or eased for a (pre or post defined) period of time.

In an embodiment, the access control system 10 comprises a radiation absorbing element 310 configured and operable to prevent emission of the X ray or gamma ray radiation out of the access control system 10.

Figure 1C:
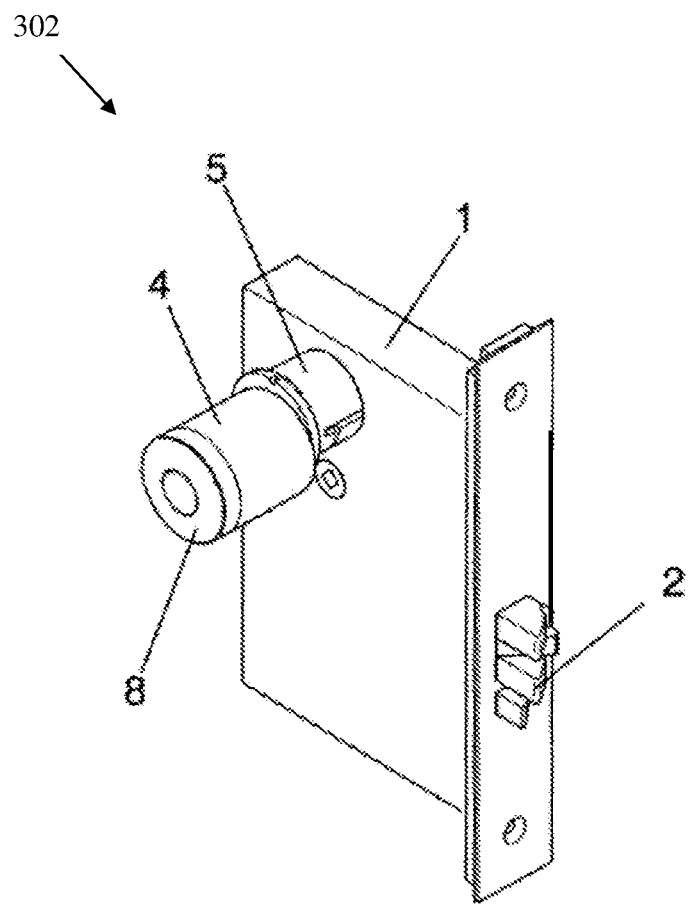
FIG. 1c is a schematic illustration of a lock module of the present invention.

Reference is made to FIG. 1c illustrating an example of a lock module of the present invention. Although for the sake of illustration, a lock module 302 to be integrated in a door is shown, it should be appreciated that other embodiments may comprise a lock mechanism external to a door or on a doorjamb. The lock module 302 may be electrical, mechanical or electromechanical. The lock module 302 is thus configured to be integrated in a door lock assembly useful to secure the door to a door jamb or other suitable fixed structure. The door can be any variety of doors used in residential, business, etc. applications that can be used to close off passageways, rooms, access areas, etc. The lock module 302 is capable of being actuated with a handle in a known fashion. It should be appreciated that the handle may be replaced with any other similar mechanism known in the art (e.g., knob). However the handle may only be engaged with the lock module if a valid XRF signature is read at the control circuit.

The lock module 302 may enclose a turnable lock cylinder and a locking mechanism which normally prevents turning of the lock cylinder with regard to the lock body and which can be moved by the access object into a releasing position allowing turning of the lock cylinder. In some embodiments, the lock module includes a control circuit configured and operable to receive a response signal from the access request receiving device and process the response signal to identify spectral features indicative of an XRF signature. The control circuit is coupled to the lock module for switching the lock module between the unlocked and locked state upon identification of the XRF signature. Therefore, the control circuit is configured as an identification and control device for receiving and identifying the XRF signature from the access object as well as an electric operating device switching the lock module between the unlocked and locked state. In some embodiments, the control circuit comprises a coupling member attached thereto and having a free position and a coupling position in which it couples the lock cylinder with the movement of the access object for opening the lock, whereby when there is a match with the XRF signature of the access object, the control circuit activates the lock module to guide the coupling member to its coupling position. The coupling member may located and may be in cooperation with a guiding groove having a guiding surface which the coupling member affects in its coupling position thereby turning the lock cylinder when the access object is turned in the lock module.

As can be seen in FIG. 1c, in a specific and non-limiting example, the lock module 302 comprises a latch 2 provided for locking and unlocking the access point in its closed state with respect to a main frame. The lock module 302 shown includes a lock casing 1, in which a latch 2 is slidably mounted. A cylinder 5 is applied to the lock module 302 with its corresponding latch 2. A cam is secured to one end of the cylinder 5 inside the casing 1 and coacts with the latch 2 to release a spring-loaded catch device mounted on the latch 2 and displace the latch 2 between projecting and withdrawn positions. The catch device operates in well-known manner to retain the latch 2 in these two positions. The latch 2 can move in to and out of the door jamb when securing the door. The latch 2 can move from a retracted position to an extended position and can include a dead position in which, for example, the latch 2 resists being retracted when tampered through force applied to the latch. The latch 2 can be moved based upon a force imparted through any one or a combination of a motor internal to the lock module 302 and an access object. The lock module 302 can include a latch driving mechanism interposed between the latch 2 and the motor such that when the motor imparts a force the latch driving mechanism is moved which consequently imparts a motion to the latch 2. A force can be transmitted via the rotor to the latch driving mechanism of the latch 2 whether through a turn of the key.

Specifically, the cylinder 5 may be an electromechanical cylinder assembly including an electronic module comprising a knob 4 being coupled to the body of the cylinder 5 and a rotor. The cylinder 5 has a hole used to receive an access object which can be used to manipulate the latch 2 to secure the door. The cylinder 5 is thus formed with a key slot having a complex cross-sectional shape as is well known in conventional mechanically operated cylinder locks. The electronic module formed by the knob 4 and rotor are axially fixed with respect to the body of the cylinder 5 and with the ability to rotate freely. The free rotation of the assembly formed by the knob 4 and the rotor without the actuation of the lock is carried out. The cylinder 5 is retained by a plunger of a solenoid device. On energization of the solenoid, the cylinder 5 can be turned by the key so that the latch 2 is driven in or out (according to the direction of turning) by the cam.

The lock module 302 may also comprise a battery mounted on a battery-holder. The lock module 302 may thus also comprise a powered module also useful in manipulating the latch 2. The powered module can include an energy source, an appropriate motor for activating the latch, associated electronic controls useful in activating the latch, etc.

The control circuit is included inside the knob 4, which also acts as an emitter irradiating the access object. The key slot actually opens on to the surface of the cylinder and this permits the radiation of the key by the emitter 4. The control circuit may engage a motor to drive the latch 2.

The different parts of the lock module can be in communication with each other using a variety of mechanisms. Though not depicted, in some embodiments a cabling can be used to connect the control circuit to the latch such that drive signals useful to extend or retract the latch can be transmitted. For example, a cable can be used to provide power to the motor from a battery device stored in the lock module and/or convey a signal, such as an actuation signal for the motor, from the control circuit. Other types of technologies can also be used in lieu of, or in addition to, such as but not limited to I button, Body Comm, Smart card, etc. Not all embodiments need include the cabling depicted. The cabling can include one or more conductors to convey power, data signals, etc.

Figure 2:
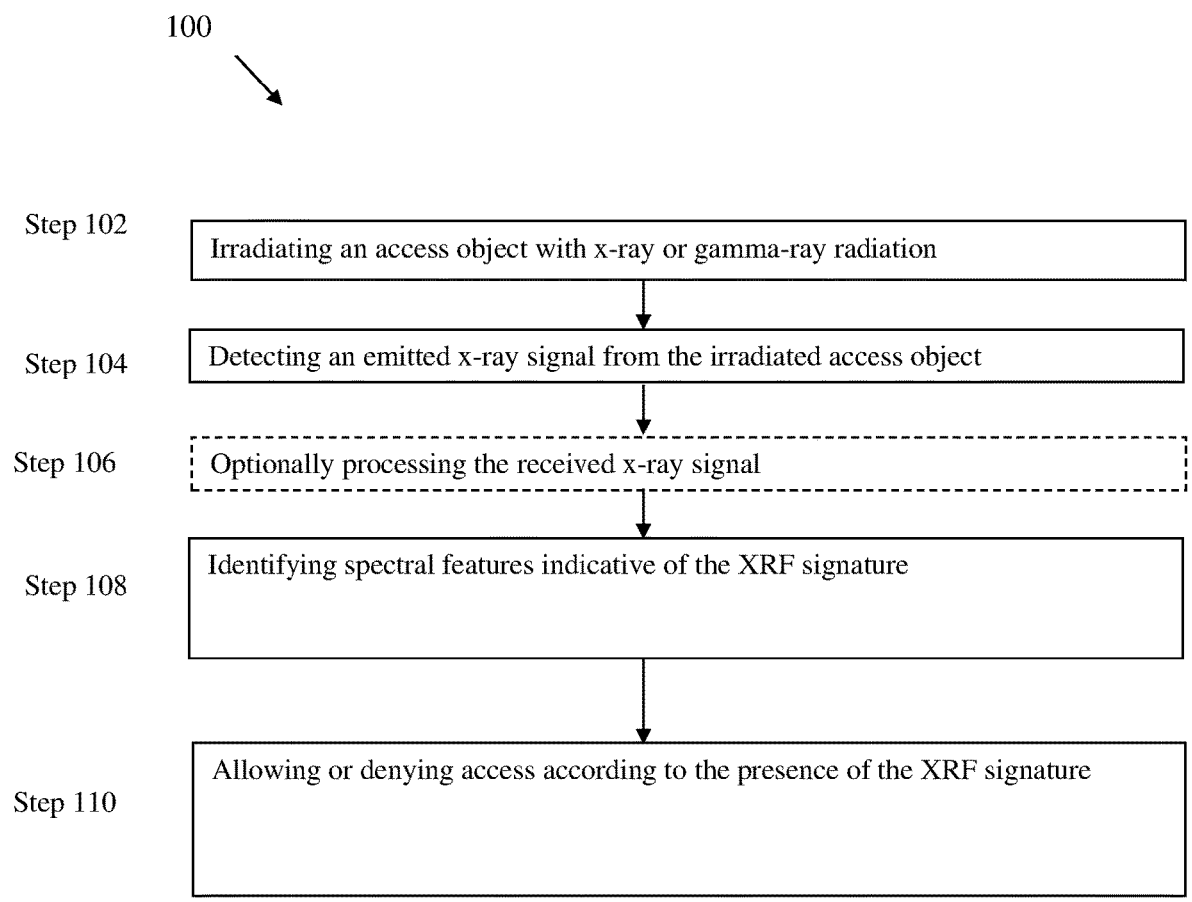
FIG. 2 is a flow chart of a method for access control according to some embodiments of the present invention.

Reference is now made to FIG. 2 which is a schematic illustration of a method, generally referenced 100, for access control according to some embodiments of the invention. In step 102, which is carried at an access point, an access object for enabling access at the access point is irradiated with an x-ray or gamma-ray radiation (i.e. primary radiation). In step 104, the signal emitted from the access object in response to the x-ray or gamma-ray irradiation signal is detected. The detection may be carried out by an XRF analyzer which includes the X-ray emitter irradiating the x-ray or gamma-ray radiation in step 102 or by a separate XRF reader. Optionally, in some embodiments, step 106 is carried out in order improve accuracy of the XRF signature subsequently obtained in step 108 as will be described below. In step 108, the identification of spectral features indicative of the XRF signature allows to determine the presence of XRF signature (e.g. authenticating signals) in the received response x-ray signal to thereby determine the authenticity of the access object. The step 108 of identification of spectral features indicative of the XRF signature may include the following processing step: analyzing the power of the response signal at one or more frequencies associated with the marking and thereby authenticating the object by determining if the response signal includes marking. The analysis may include for example performing spectral analysis to determine the power spectra of the response signal in a certain frequency band overlapping with the frequencies of the marking, and/or is may be specifically designed to detect/determine the power of the response signal at the specific one or more frequencies of the marking.

In other embodiments, the identification of the XRF signature may include processing the detected XRF response signal, or the enhanced response signal (being the detected XRF response signal filtered/processed as will be described below), and determining the amounts/concentration (e.g., in ppm) of the XRF markers included therein. For example, the control circuit is also configured to compare the measured concentrations with the concentrations derived from the preselected signature which is stored in the database, and determine its authenticity accordingly.

In step 110, access is allowed or denied according to the presence of the XRF signature in the response x-ray signal.

If the received access object(s) are determined to be authorized access objects (e.g., the access object is valid and useable for the emitter during the time at which the access was read by the access request receiving device), then the control circuit will open the lock module or engage the lock mechanism with the handle, thereby allowing a user to open the lock module. If the received access objects are not determined valid (or were determined to be invalid), then the control circuit may not perform any action or the control circuit may proactively indicate that the access object(s) were invalid. For instance, the control circuit may sound an alarm, send a notification to security personnel, store information in an activity log about the invalid access objects, light an indicator, etc.

In some embodiments, in step 106, the received x-ray signal is processed in order to reduce noise and/or clutter (radiation from foreign materials in the vicinity of the metallic object) caused, for example, by back-scattering, instrumental noise of the detection device and foreign materials in the vicinity of the access object. This processing step may also include amplifying and/or enhancing the received signals relatively to the background. However, naïve filtration of the background and/or the noise, for example by using common methods such as quasi-Gaussian spectroscopy amplifier and Gaussian filtering may also significantly reduce all or part of the authentication signals. Hence, more advanced signal processing methods should be employed. For example, the received x-ray signal may be processed using statistical methods such as time series analysis as disclosed for example in U.S. provisional patent application No. 62/142,100 which is incorporated herein by reference.

In some embodiments, step 102 comprises irradiating the object with x-ray or gamma-ray radiation to read and identify the XRF signature of the access object for controlling access at an access point and for key control purposes (e.g. preventing unauthorized key duplication as will be described below).

Method 100 may be used as an added security measure for preventing unauthorized access, additionally, it may be used as a measure for adding flexibility in controlling and managing access. For example, a set of keys or other access objects associated which one or more lock modules or access points, includes a plurality of subsets of access objects each marked with a different XRF signature wherein each subset of access objects is provided with a different access permits. For example, a subset of access object may enable access only at certain hours of the day (e.g. during the day time but not at night) while a different subset enable may enable access at different hour or at all time.

In an embodiment, both the lock module or access point and the access object are marked with XRF signature. The XRF signatures of the access object and the lock module/access point may be identical or matching. In an embodiment of method 100 the XRF signatures of both the access object and the lock module/access point are read (for example, by a portable XRF analyzer) and access is allowed if these XRF signatures match.

Figure 3:
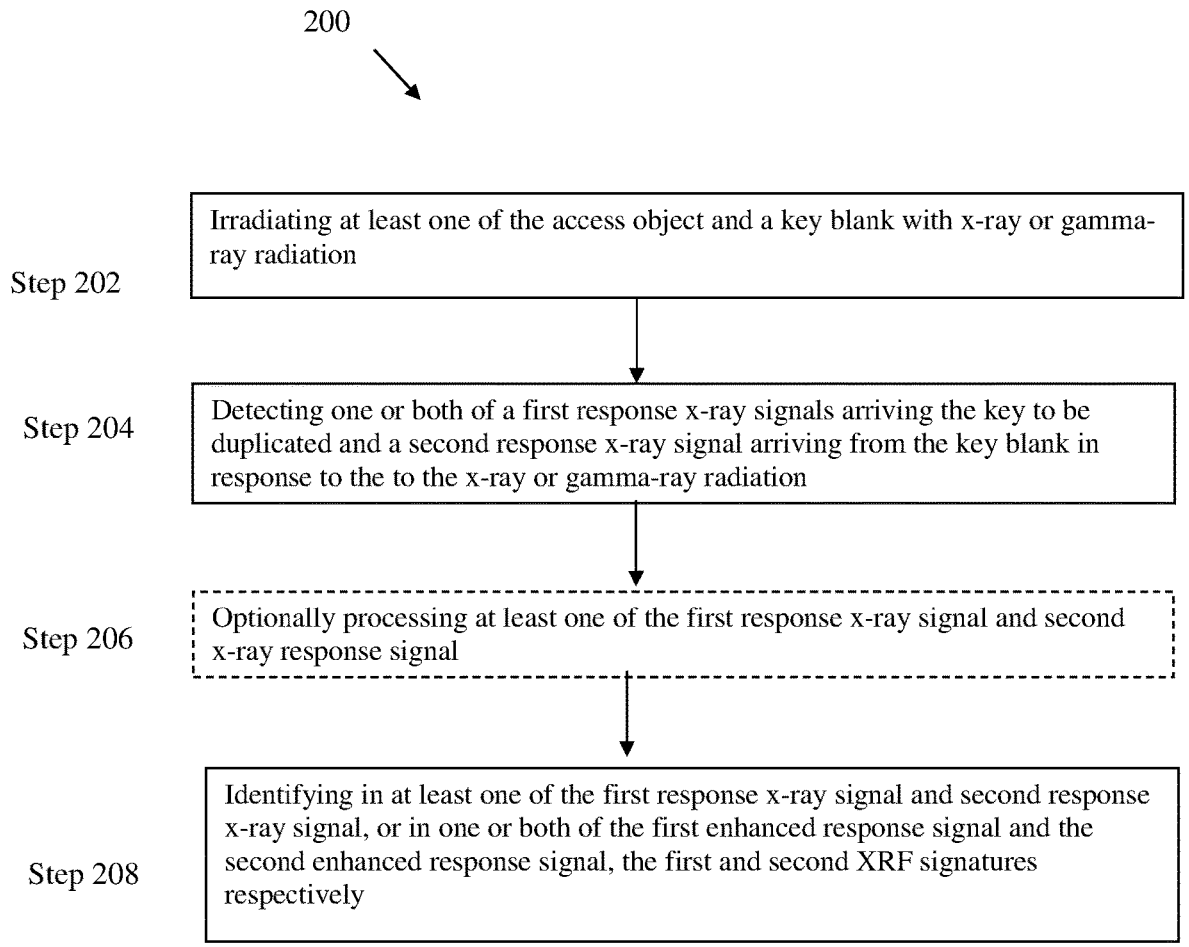
FIG. 3 is a flow chart of a method for preventing unauthorized key duplication according to some embodiments of the present invention.

In addition to access control purposes, the access object can be used also for preventing unauthorized duplication. Reference is now made to FIG. 3 which is a schematic illustration of a method, generally referenced 200, for preventing unauthorized duplication of a key using a key blank. According to method 200, the access object to be duplicated and/or the key blank used for duplication, may be marked by XRF signature, and duplication would be permitted according to whether the XRF signature is identified by XRF analysis. The access object to be duplicated (hereinafter the key) may be marked by a first XRF signature, and the key blank may be marked by a second or the same XRF signature. In step 202, the access object and/or the key blank are irradiated by x-ray or gamma-ray radiation. In step 204, a first response x-ray signal arriving from the access object and a second response x-ray signal arriving from the key blank are detected. Both steps 102 and 104 may be carried out by a single device such as an XRF analyzer which includes both an x-ray or gamma ray emitter and a detector. The emitter emitting the x-ray or gamma-ray radiation and the detector detecting the response signals may be incorporated in a key duplication assembly. Optionally, in some embodiments step 206 is carried out in order to improve the accuracy of the XRF signature subsequently obtained in step 208 described below. In step 206, at least one of the first x-ray response signal and the second x-ray response signal is processed so as to improve the SNR and/or SCR of the x-ray signals obtained in step 204. The processing may include for example statistical processing, such as time series analysis for removing at least one of the trend and/or periodic components from the spectral profile (e.g. from the power spectrum) of the detected x-ray response signals, and is similar to the processing method of step 106 in method 100. It should be noted that such processing aimed at improve the accuracy of the XRF signature by improving the SNR and/or SCR of the x-ray signals previously obtained can also be performed in the processing method of step 106 in method 100. In step 208 the first XRF signature of the access object is identified in the first response x-ray signal or, in the case step 206 is carried out, in the enhanced response signal. The identification of the XRF signature is similar to the identification method of step 108 in method 100. Alternatively, or additionally the second XRF signature of the key blank is identified in the second response x-ray signal or, if step 206 is carried out, in the second enhanced response signal. Subsequently, authorization to duplicate the key using the key blank is provided according presence of the first and second XRF signatures in their respective response x-ray signals or enhanced response signals. Since the XRF signature is carried by the access object itself, in duplicating an access object according to method 200 there is no need for additional information to be presented or inputted to the duplication assembly (e.g. a code that is punched in using a keypad, or carried by swipe card or a memory device).

In some embodiments, the access control system comprises a module device being an access object duplication assembly adapted to enable duplication of the coded physical or electrical pattern in the first codable part (illustrated in FIG. 1b), upon receiving an unlocking signal generated by the control circuit.

In some embodiments only the key blank is interrogated and examined by XRF analysis and duplication of the key is permitted only if the key blank carries an appropriate XRF signature. Such a mode of operation may be suitable for verifying that only suitable key blanks are used for duplicating preselected key types (e.g. manufactured by specific manufacturers).

In some embodiments only the access object is interrogated and examined by the XRF analysis and duplication is selectively restricted in accordance with the XRF signature carried by the access object. For example, within a set of access objects associated with a lock module/access point a subset may be marked by a preselected XRF signature which enables duplication, whereas the rest of the set is not marked or alternatively marked by a different XRF signature for which duplication is not permitted.

The invention claimed is:
1. An access control system comprising:
an access request receiving device being configured and operable for receiving an access object being capable of carrying a coded pattern corresponding to at least one lock module and a XRF signature; said access request receiving device comprising an emitter configured and operable for irradiating said access object with a radiation having a wavelength in the range of about $10^{-12}$ and $10^{-9}$ m and a detector configured and operable for detecting a response signal from the irradiated access object;

a lock module operable between an unlocked state and a locked state and vice versa a control circuit being configured and operable to receive the response signal from the access request receiving device and process the response signal to identify spectral features indicative of an XRF signature of said access object; wherein said control circuit is adapted to receive data indicative of a correspondence between said coded pattern and said XRF signature to thereby determine whether a match exists between said XRF signature and said coded pattern, and upon determining said match to generate an unlocking signal for switching said lock module between a locked state and an unlocked state.

2. The access control system of claim 1, wherein at least one of said access request receiving device and said control circuit are at least partially disposed within the lock module.

3. The access control system of claim 1, further comprising a radiation absorbing element configured and operable to prevent emission of said radiation out of said access control system.

4. The access control system of claim 1, further comprising a housing, wherein said control circuit, said access request receiving device, and said lock module are housed in said housing.

5. The access control system of claim 1, wherein said lock module includes a motor mechanically coupled to a latch mechanism for locking and unlocking the latch mechanism, thereby switching said lock module between the unlocked and locked state.

6. The access control system of claim 5, wherein said control circuit comprises a coupling member configured and operable to control said motor.

7. The access control system of claim 1, further including a processor coupled to said access control system, the processor being configured for communicating with said lock module and for modifying XRF signatures list associated with user access stored within said control circuit.

8. The access control system of claim 1, wherein said lock module is integrated within a door.

9. The access control system of claim 8, wherein said lock module is adapted to fit within an aperture formed in a door for a standard mechanical lock.

10. The access control system of claim 1, further comprising an access object having an XRF signature corresponding to a certain lock module.

11. The access control system of claim 10, wherein said access object is a key comprising a coded physical or electrical pattern for opening said lock module; and said database includes data indicative of said coded physical or electrical pattern corresponding to a certain XRF signature.

12. The access control system of claim 10, wherein said access object comprises a first codable part adapted for carrying a coded physical or electrical pattern corresponding to a lock module, and a second codable part carrying at least one XRF marker embedded therein and defining said XRF signature to be matched with said lock module.

13. The access control system of claim 10, further comprising an access object duplication assembly adapted to enable duplication of said coded physical or electrical pattern in said first codable part, upon receiving said unlocking signal generated by said control circuit.

14. An access object comprising a first codable part adapted for carrying a coded physical or electrical pattern corresponding to a lock module, and a second codable part carrying at least one XRF marker embedded therein and defining an XRF signature to be matched with said lock module to enable unlocking said lock module based on a matching between said coded physical or electrical pattern and said XRF signature, wherein said XRF signature includes information about at least one of a depth of key cuts defining a key combination, physical characteristic of the key, configuration of a key profile.

15. The access object of claim 14, further comprising at least one of keys, key blanks, locks, access cards, access badges, tickets, and Id documents such as passports, identification cards.

16. An access object comprising:
a first codable part adapted for carrying a coded physical or electrical pattern corresponding to a lock module;
a second codable part carrying at least one XRF marker embedded therein and defining an XRF signature to be matched with said lock module to enable unlocking said lock module based on a matching between said coded physical or electrical pattern and said XRF signature;
at least one of keys, key blanks, locks, access cards, access badges, tickets, and Id documents such as passports, identification cards; and
a metallic key having plastic grip, wherein the metallic key and the plastic grip has the same XRF signature.

17. A method for access control comprising:
irradiating an access object with radiation having a wavelength in the range of about $10^{-12}$ to $10^{-9}$ m;
detecting a response signal from the irradiated access object;
identifying in the response signal spectral features indicative of an XRF signature; and
generating an unlocking signal for switching a lock module between a locked state and an unlocked state upon identification of said XRF signature, wherein the method further comprises at least one of: enabling access upon identification of the XRF signature; switching a lock module between an unlocked state and a locked state and vice versa; modifying a XRF signatures list associated with user access; securing a door; receiving data indicative of a correspondence between a coded pattern carried by said access object and said XRF signature, to thereby determine a match between said XRF signature and said pattern; upon identification of the XRF signature comprising preventing unauthorized key duplication.

* * * * *